United States Patent
Wink

(10) Patent No.: US 7,403,591 B2
(45) Date of Patent: Jul. 22, 2008

(54) ALTERNATIVE ACQUISITION SCHEME FOR CORONARY ANGIOGRAPHY

(75) Inventor: Onno Wink, Denver, CO (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 11/573,561

(22) PCT Filed: Aug. 2, 2005

(86) PCT No.: PCT/IB2005/052589

§ 371 (c)(1),
(2), (4) Date: Feb. 12, 2007

(87) PCT Pub. No.: WO2006/018768

PCT Pub. Date: Feb. 23, 2006

(65) Prior Publication Data

US 2007/0253527 A1    Nov. 1, 2007

Related U.S. Application Data

(60) Provisional application No. 60/601,292, filed on Aug. 13, 2004.

(51) Int. Cl.
*G01N 23/04* (2006.01)
(52) U.S. Cl. .................... 378/62; 378/205
(58) Field of Classification Search ......... 378/193–197, 378/62, 205
See application file for complete search history.

(56) References Cited

U.S. PATENT DOCUMENTS

| | | |
|---|---|---|
| 5,038,371 A | 8/1991 | Janssen et al. |
| 5,155,757 A | 10/1992 | Sakaniwa et al. |
| 6,113,264 A | 9/2000 | Watanabe |
| 6,196,715 B1 | 3/2001 | Nambu et al. |
| 6,351,513 B1 | 2/2002 | Bani-Hashemi et al. |
| 6,389,104 B1 | 5/2002 | Bani-Hashemi et al. |
| 6,577,889 B2 | 6/2003 | Ichihashi |
| 6,687,331 B1 | 2/2004 | Mueller et al. |
| 6,744,848 B2 | 6/2004 | Stanton et al. |
| 2001/0054695 A1 | 12/2001 | Lienard et al. |
| 2003/0048935 A1 | 3/2003 | Keren |
| 2003/0069499 A1* | 4/2003 | Lienard et al. ............... 600/431 |

(Continued)

FOREIGN PATENT DOCUMENTS

DE    2539397 A1    5/1977

(Continued)

OTHER PUBLICATIONS

Kuon, E., et al.; Usefulness of rotational spin for coronary angiography in patients with advanced renal insufficiency; Amer. J. of Cardiology; 2002; vol. 90; pp. 369-373.

(Continued)

*Primary Examiner*—Hoon Song

(57) ABSTRACT

A control processor (30) causes the drives (22, 24, 26) of a mechanical arm scanner to move an x-ray source (12) and a detector along an elliptical trajectory (50). The trajectory can be customized (38) to deviate from a true mathematical ellipse or to be only an arc segment. As the x-ray source and detector move along the trajectory, a large multiplicity of projection images are generated, at least when a contrast agent is present in the region-of-interest. A selectable limited subset of the generated projection images are selected for display in order to make an angiographic diagnosis.

19 Claims, 2 Drawing Sheets

U.S. PATENT DOCUMENTS

2003/0147504 A1* 8/2003 Hanover ................ 378/197
2005/0249327 A1 11/2005 Wink et al.

OTHER PUBLICATIONS

Maddux, J. T., et al.; Randomized study of the safety and clinical utility of rotational angiography versus standard angiography in the diagnosis of coronary artery disease; Catherization and Cardiovascular Interventions; 2004; 62:167-174.

Maddux, J. T., et al.;Rotational angiography and 3D coronary modeling: revolutions in the cardiac cath lab; MedicaMundi; 2003; 47(2)8-14.

Tommasini, G., et al.; Panoramic coronary angiography; JACC; 1998; 31(4)871-877.

* cited by examiner

ALTERNATIVE ACQUISITION SCHEME FOR CORONARY ANGIOGRAPHY

CROSS REFERENCE TO RELATED APPLICATIONS

This application claims the benefit of U.S. provisional application Ser. No. 60/601,292 filed Aug. 13, 2004, which is incorporated herein by reference.

The present invention pertains to the diagnostic imaging arts. It finds particular application in conjunction with coronary angiography for visualizing the left coronary system and will be described with particular reference thereto. However, it is to be appreciated that the present invention may also find application in conjunction with the right coronary system, other parts of the circulatory system, and other anatomical features.

Traditionally, in coronary angiography of the left coronary system, four projection views are generated at four viewing angles. Although there are four generally accepted textbook viewing angles, many radiologists prefer to take the four views at somewhat different viewing angles. Some prefer to take views at more than four viewing angles. Also, if the view at the selected viewing angle does not convey the desired information, (e.g., two arteries could overlap in the region of interest making the evaluation of one of the arteries ambiguous) then views at additional viewing angles are generated. To generate the views at each viewing angle, a mechanical arm which carries an oppositely disposed x-ray source and detector is positioned at each of the four viewing angles. When the mechanical arm is in position to image at the first of the viewing angles, the patient is injected with a contrast agent and one or more views at that viewing angle are generated. After acquiring the image in the first position, the contrast agent injection is terminated, and the mechanical arm is then positioned to image at the next viewing angle. The patient is again injected with a second dose of contrast agent and imaged, and the process repeated. In this manner, the patient is given four or more doses of contrast agent corresponding to each imaged viewing angle. Such high dosages of the contrast agent are undesirable, since the contrast agent may be a physiologically damaging substance.

In one example technique to reduce contrast agent dosage, the mechanical arm is positioned to define a skewed plane through the region of interest. When the patient is injected with the contrast agent, the mechanical arm is rotated in an arc of about 120° along the skewed plane to generate a large number of images, e.g., 120 images. The skewed plane is selected such that it substantially intersects two of the four conventional viewing points. The mechanical arm is then positioned to define a skewed plane in the opposite direction, and the process is repeated to generate about another 120 images along the second skewed plane. The second skewed plane is defined such that it substantially intersects the other two conventional viewing angles. In this manner, views along the four conventional viewing angles can be generated with only two doses of contrast agent. Even though each dose is slightly larger, there is still about a 30% reduction in contrast agent dosage.

Although a marked improvement, it would still be desirable to reduce the contrast agent dosage even more.

According to one aspect, a diagnostic imaging method is provided. An x-ray source and an x-ray detector are moved continuously along at least a segment of an ellipse. A multiplicity of projection images are generated during the moving of the source and detector including a plurality of projection images at different angles through the region of interest. A plurality of the images generated along the elliptical trajectory are selected.

According to another aspect, a diagnostic imaging apparatus is provided. The apparatus includes a means for moving an x-ray source and an x-ray detector continuously along at least a segment of an ellipse. A means for generating a multiplicity of projection images during the moving generates a plurality of projection images at different angles through the region of interest. A means is provided for selecting a plurality of the images generated along the elliptical trajectory for display for diagnostic imaging purposes.

According to yet another aspect, a diagnostic imaging method is provided, which employs a mechanical arm to image an imaging subject at selected viewing positions defined by a cranial or caudal viewing angle and a left or right anterior oblique viewing angle. A continuous trajectory of selected viewing positions is traversed by adjusting both the cranial or caudal viewing angle and the left or right anterior oblique viewing angle during the traversing. Images of the imaging subject are acquired during the traversing.

One advantage resides in reducing the contrast agent dosage administered to the patient.

Another advantage resides in generating views at a multiplicity of viewing angles without additional contrast agent exposure.

A yet further advantage is that it is not necessary to coordinate initialization and termination of x-ray detector movement and contrast agent injection.

Still further advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
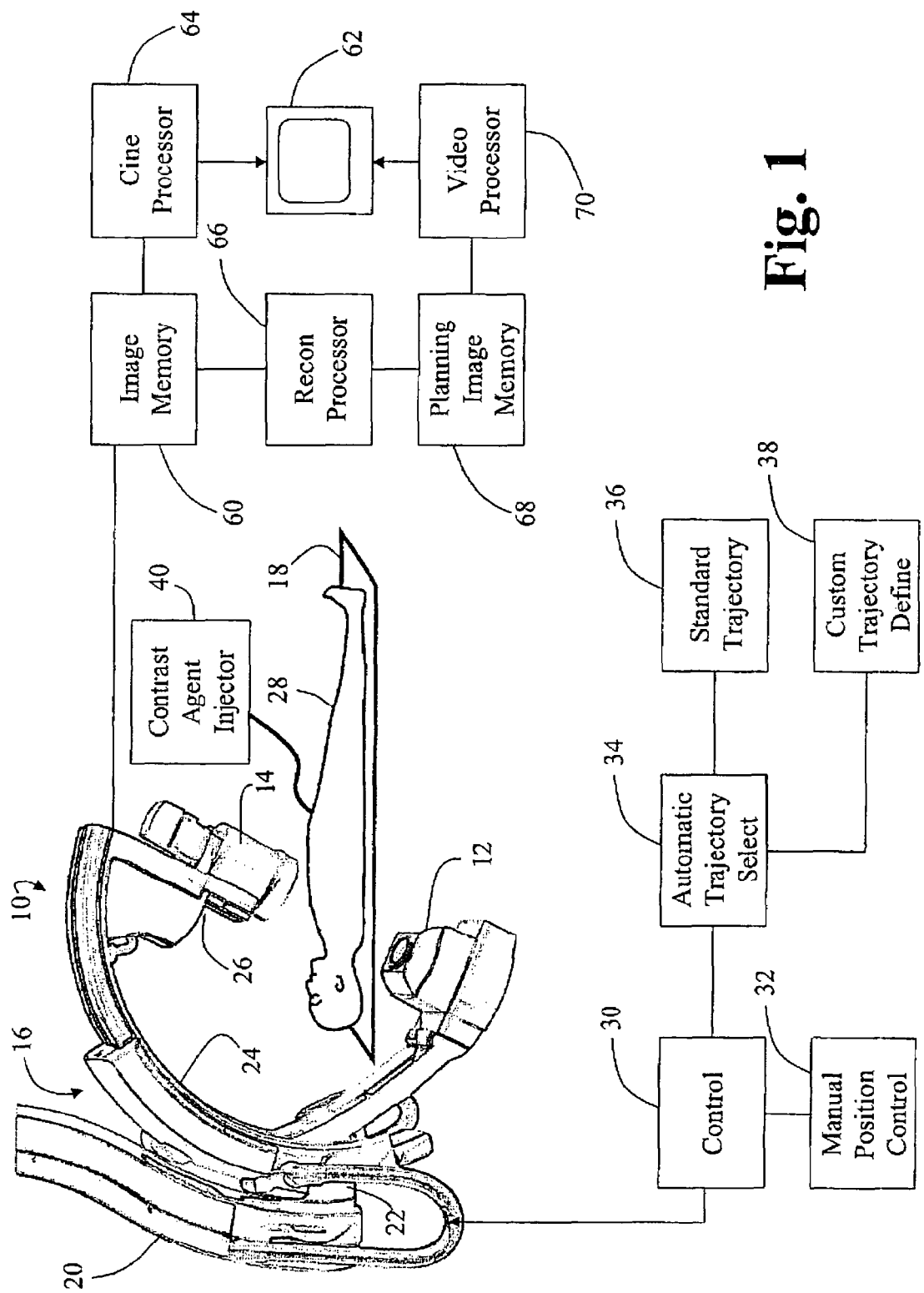
FIG. 1 is a diagrammatic illustration of a coronary angiography imaging system employing a mechanical arm to image at selected viewing positions.

With reference to FIG. 1, a cardiovascular x-ray scanner 10 includes an x-ray tube or other x-ray source 12 and an x-ray detector 14. In the illustrated embodiment, the x-ray detector 14 includes an image intensifier system, although solid state flat panel detectors, video cameras, and other types of x-ray detectors are also contemplated. The x-ray source 12 and detector 14 are positioned on opposite sides of a subject-receiving surface 18 by a mechanical arm 16. The illustrated mechanical arm 16 is known in the art as a G-arm. In other embodiments, another mechanical arm providing suitable angular control of the x-ray source and detector may be used, such as a C-arm. Typically, a C-arm provides greater angular range than a G-arm. The mechanical arm 16 preferably has a robust stability that enables precise positioning and high reproducibility, resulting in high quality images. The mechanical arm 16 is rotatably mounted on a stationary gantry 20. In the illustrated embodiment, the stationary gantry 20 is ceiling-mounted; in other embodiments, the stationary gantry is floor-mounted.

The mechanical arm assembly includes a controllable rotary drive 22 for controlling rotation of the mechanical arm about a horizontal axis in or parallel with the plane of the subject support 18. A tilt drive 24 causes the mechanical arm assembly to tilt the trajectory between the x-ray source 12 and the detector 14 in a plane containing the source 12, detector 14, and mechanical arm 16. A detector positioning drive 26 enables movement of the detector 14 closer to or further away from the x-ray source 12.

For coronary angiography, a patient 28 is placed on the subject support 18. In the illustrated arrangement of the patient 28, the rotary drive 22 adjusts the position of the mechanical arm 16 to provide a selected left or right anterior oblique view angle, while the tilt drive 24 adjusts the position of the mechanical arm 16 to provide a selected cranial or caudal view angle. The detector positioning drive 26 optionally moves the detector head 14 toward or away from the patient 28 to maximize signal. In other embodiments, the patient is arranged in the orthogonal direction, in which arrangement the rotary drive 22 adjusts the cranial or caudal view angle and the tilt drive 24 adjusts the left or right anterior view angle.

A control processor 30 controls the drives 22, 24, and 26 and the x-ray tube 12 to move the x-ray source 12 and detector 14 along a selected trajectory of views defined by selected cranial or caudal view angles and selected left or right anterior view angles. The controller 30 further operates the x-ray source 12 at appropriate times during the movement to obtain images. A position controller 32, which may be any type of manually operable input device, is manipulated by a radiologist or technician to position the mechanical arm 16 with the radiation source 12 and detector head 14 in selected positions.

An automatic trajectory selection means 34, such as a computer generated look-up table, enables the operator to select one of a plurality of standard trajectories stored in a standard trajectory memory 36 or to select a custom defined trajectory 38. For example, the operator may select a standardized trajectory and use the customize trajectory defining means to customize the trajectory. This might be done in numerous ways, such as by displaying the trajectory on a graphical user interface and allowing the operator to push or pull portions of the trajectory with a cursor. Other options include permitting the operator to define the trajectory mathematically, programmatically, or the like.

The trajectory is suitably defined by a timed sequence of viewing positions each specified by a cranial or caudal viewing angle and by a left or right anterior oblique viewing angle. The cranial or caudal viewing angle is suitably identified by a setting of the tilt drive 24, for example with increasingly positive tilt settings corresponding to increasing caudal viewing angles, and increasingly negative tilt settings corresponding to increasing cranial viewing angles. Similarly, the left or right anterior oblique viewing angle is suitably identified by settings of the rotary drive 22, for example with increasingly positive rotary settings corresponding to increasing right anterior oblique viewing angles, and increasingly negative rotary settings corresponding to increasing left anterior oblique viewing angles.

For coronary angiography, a suitable contrast agent is administered to the patient 28 by a contrast agent injector 40 before imaging. Typically, the contrast agent injector 40 injects a controlled flow of contrast agent into the bloodstream of the patient 28 intravenously, so that blood-filled arteries and veins appear with enhanced contrast in the images. The effect lasts only as long as the contrast agent remains in the portion of the bloodstream being imaged; once the contrast agent flow into the bloodstream is terminated, the vascular contrast rapidly degrades.

Figure 2:
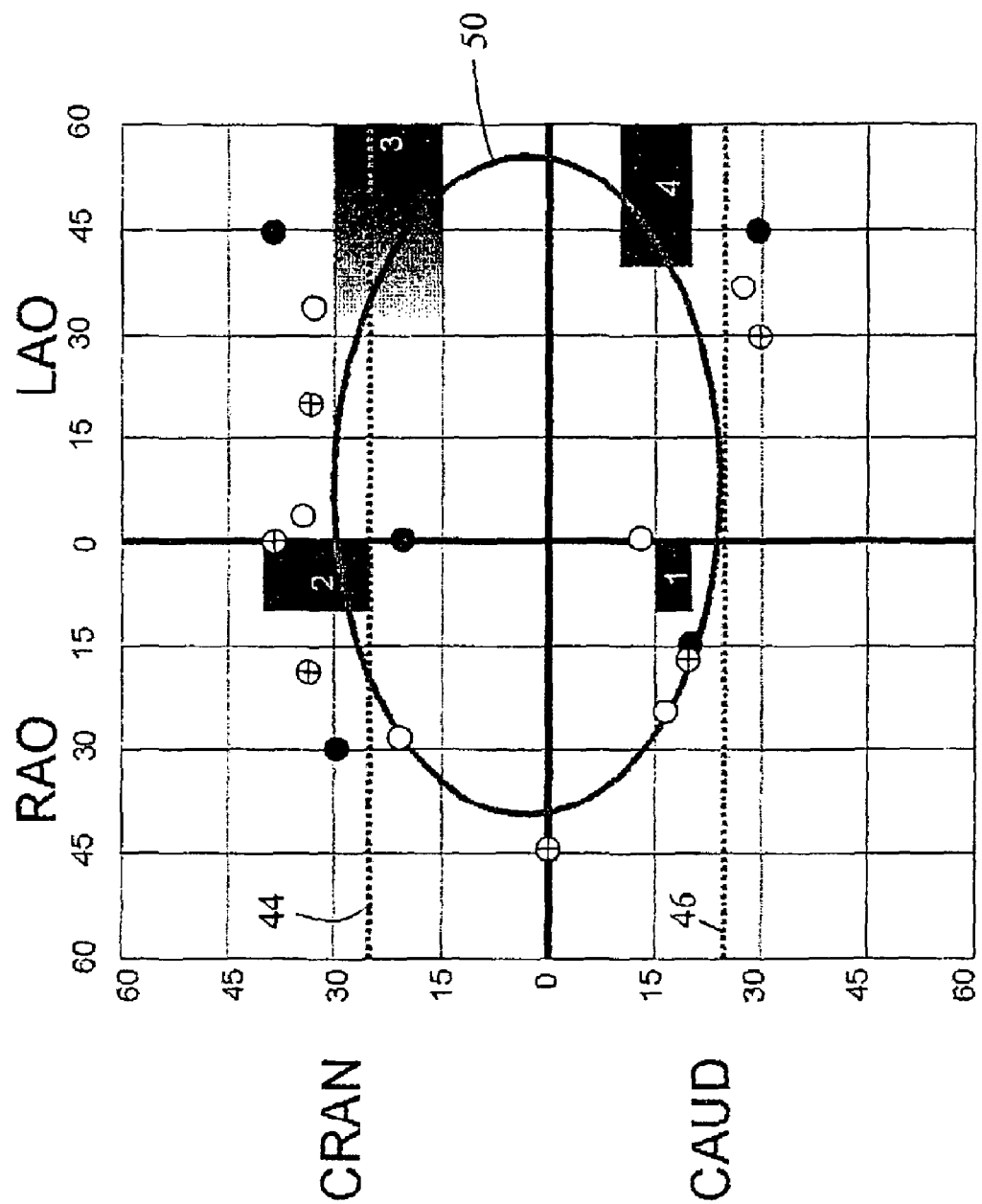
FIG. 2 is a view map displaying suitable acquisition positions and acquisition trajectories executable by the imaging system of FIG. 1.

With reference to FIG. 2, some suitable trajectories for coronary angiography are described. In FIG. 2, the vertical coordinate is the cranial or caudal viewing angle controlled in the embodiment of FIG. 1 by the tilt drive 24, and the horizontal coordinate is the left or right anterior oblique viewing angle controlled by the rotary drive 22. Other mechanical arms may use different drive motors for setting the cranial or caudal viewing angle and for setting the left or right anterior oblique viewing angle. In FIG. 2, the black regions labeled "1", "2", "3", and "4" identify the four conventional viewing angles for left coronary angiography. Standard position "1" is located at approximately a caudal viewing angle of 15-20° and a right anterior oblique viewing angle of about 0-10°. Standard position "2" is located at approximately a cranial viewing angle of 25-40° and a right anterior oblique viewing angle of about 0-10°. Standard position "3" is located at approximately a cranial viewing angle of 15-30° and a left anterior oblique viewing angle of about 30-60°. Standard position "4" is located at approximately a caudal viewing angle of 10-20° and a left anterior oblique viewing angle of about 10-20°.

The operator can position the source 12 and detector 14 in any of these standard positions using the manual position controller 32. However, various radiologists prefer different viewing angles. As three examples, viewing angles preferred by one radiologist are denoted by open circles ("○") in FIG. 2, viewing angles preferred by another radiologist are denoted by filled circles ("●"), and viewing angles preferred by yet another radiologists are denoted by open circles inscribed with a plus sign ("⊕"). In each of these sets of preferred viewing angles, the imaging proceeds as follows. First, the mechanical arm 16 is manipulated using the drives 22, 24 to the first viewing angle. Next, the contrast agent injector 40 is activated to initiate flow of contrast agent into the bloodstream. After a suitable time interval for inflow of contrast agent, the controller 30 initiates imaging at the selected viewing position. Once one or more images at that viewing position are acquired, flow of contrast agent is terminated. The mechanical arm 16 is manipulated using the drives 22, 24 to the next viewing angle, the contrast agent injector 40 is activated to initiate flow of contrast agent into the bloodstream, imaging is performed, and the contrast agent flow is terminated. This sequence is repeated for each viewing angle in the set of viewing angles. Thus, the patient 28 receives as many contrast agent injections as there are viewing angles in the set of viewing angles. Moreover, if it turns out that one of the preferred viewing angles is obstructed by bone or other x-ray absorbing tissue, then still more viewing angles must be acquired, entailing additional contrast agent injections.

As another option, the operator may use a trajectory selection means 34 to select linear trajectories 44, 46 in which the radiation source and detector traverse each of two oppositely skewed planes. The linear trajectory 44 is performed by varying the left or right anterior oblique viewing angle while maintaining a constant cranial viewing angle of about 20° to 25°, and passes through the standard positions "2" and "3". The linear trajectory 46 is performed by varying the left or right anterior oblique viewing angle while maintaining a constant caudal viewing angle of about 20°, and passes through the standard positions "1" and "4". In this approach, the first linear trajectory 44 is initiated by positioning the mechanical arm 16 at one end of the linear trajectory (for example, at an initial 30° cranial, 60° right anterior oblique viewing position. The contrast agent injector 40 is activated to initiate flow of contrast agent into the bloodstream. The linear trajectory 44 is then performed while simultaneously imaging. In one specific embodiment, images are acquired at 30 frames/second and the linear trajectory spans 120° over 4 seconds, providing one image every 1°. The contrast agent is terminated, and the mechanical arm 16 is moved to an initial position of the linear trajectory 46, for example to 30° caudal, 60° left anterior oblique viewing position. The contrast agent injector 40 is again activated to initiate flow of contrast agent into the bloodstream, and the linear trajectory 46 is performed while simultaneously imaging. This approach typically involves two contrast agent injections.

Additionally, the trajectory memory 36 defines an elliptical orbit or trajectory 50 which passes through or close to typical radiologist-preferred and conventional viewing angles. When this trajectory is initiated by the operator, the mechanical arm moves the radiation source 12 and detector 14 around the elliptical orbit 50. In this approach, contrast agent flow is initiated, followed by execution of the elliptical orbit 50, followed by termination of contrast agent flow. The elliptical path 50 can acquire a complete set of coronary angiography images with a single contrast agent injection. Optionally, the trajectory memory 36 may include a series of elliptical trajectories which more closely match the preferred viewing angles of various radiologists to provide an optimized generally elliptical trajectory for each radiologist. Moreover, although the trajectories are referenced as elliptical, it is appreciated that when customizing their standard trajectory, each radiologist may depress or extend their trajectory to have smoothly varying depressions or lumps. For example, the custom elliptical trajectory for the radiologist who prefers view angles indicated by the filled circles ("•") may be stretched to define a smooth curve which passes through or close to each of those viewing angles. Additionally, the elliptical pattern need not be complete, that is, the operator may wish the detector 14 and source 12 to undergo a partial ellipse that captures all points of interest they wish to review. In some instances, non-standard viewing positions are advantageous. For example, after a heart transplant non-standard viewing positions are sometimes suitable. Similarly, the viewing positions may be shifted for large, small, obese, or other atypical patients. The trajectory 50 can encompass such typical variations in optimal viewing positions.

Although the elliptical path 50 can image using a single injection of contrast agent, more than one contrast agent injection can be used. For example, multiple injections can be used in conjunction with cardiac gating, where the contrast agent injections and x-ray dose are timed based on an electrocardiographic signal. Moreover, because the elliptical path 50 forms a closed loop path, it can be repeatedly cycled without stopping between each traversal of the path to reposition the mechanical arm 16 at the initial position. The ability to cycle the trajectory provides the clinician with more freedom to choose when to inject and when to stop injecting. For some diagnoses, it is convenient for the operator to run the path back and forth, that is, from a starting point to a finishing point and then reversing to go back to the starting point, so that the operator can more easily follow a part of a vessel.

In some embodiments, the detector positioning drive 26 is used to move the detector 14 during the traversal of the elliptical trajectory 50 so as to minimize the distance between the source 12 and detector 14 throughout the trajectory 50. For this purpose, a second positioning drive (not shown) is optionally provided to adjust the distance of the radiation source 12 from the patient 28. For example, in addition to the elliptical movement of the detector 14 and x-ray source 12, the radiologist may define a distance between the detector 14 and the source 12. This variable may vary from patient to patient, as patients with more girth may be required to have a greater distance between the detector 14 and the source 12 than more svelte patients. By controlling the distance between the source 12 and the detector 14, the amount of scatter radiation received by the operator is reduced. In some embodiments, an optical, capacitive, or other sensor is disposed on the detector 14 to detect obstructions in the detector's 14 path, such as the patient or the operator. In such embodiments, the detector-to-patient distance (and/or source-to-patient distance) can be feedback-controlled. These distances may also depend on the type of reconstruction, and whether it is more advantageous to have the detector 14 and the source 12 closer together or farther apart. It is to be understood that the distance between the detector 14 and the source 12 does not have to be constant as the elliptical path 50 is traversed, The operator can vary the distance as a function of time, or as a function of the patient, as the instant application and space allow.

As the x-ray source 12 and detector 14 are rotating around the elliptical trajectory 50, the x-ray tube generates x-rays and the detector 14 detects x-ray intensities after transmission through the patient 28 generate projection images which are communicated and stored in an image memory 60. In one specific embodiment, the mechanical arm assembly 16 moves around an elliptical trajectory in about 6 seconds and generates 30 images per second. More generally, the mechanical arm 16 may traverse the trajectory faster or slower and the frame rate at which the images are generated may be faster or slower. In some embodiments, the elliptical trajectory 50 is initiated before or at about the same time as the contrast agent injector 40 initiates inflow of contrast agent, and the trajectory is traversed at least once before the contrast agent reaches the imaged region to generate a baseline set of images. The traversing of the trajectory continues as the contrast agent enters and builds in the region-of-interest. At least one trajectory is generated while the contrast agent is at full strength in the region-of-interest. Optionally, the mechanical arm 16 continues to rotate around the elliptical orbit as the contrast agent is flushed out of the region-of-interest until an ending set of images is generated with no contrast agent. In this manner, the image memory 60 is loaded with a series of images from various angles with images at each of the angles depicting the build-up, full contrast agent strength, and contrast agent washing-out.

The operator may pick various viewing angles along the trajectory and view these images from the selected viewing angles on a graphical user interface 62. Alternately, the operator may use a ciné processor 64 to cause the series of images around the trajectory to be displayed serially to assist the radiologist in selecting the best viewing angles. The operator can also control the ciné processor to display all of the images generated at the same viewing angle sequentially to illustrate the temporal evolution of the contrast agent in the region of interest. As yet another option, a reconstruction processor 66 can reconstruct the data generated along the trajectory into a three-dimensional image representation of the region of interest which is stored in a three-dimensional planning image memory 68. The operator controls a video processor 70 to withdraw selected portions of the image for display.

Of course, numerous combinations of displays are contemplated. One contemplated system includes two black and white progressive display monitors in the examination room suspended from the ceiling, giving an operator maximum accessibility while minimizing obtrusiveness. An LCD color monitor and a black and white CRT monitor are two suitable image display devices for use in the control room. In some embodiments, the progressive display monitors are replaced by black and white or color LCD monitors in both the control room and the examination room. Optionally, a second reference monitor in the examination room can display both reference images and reference runs, and a user interface on the second reference monitor is accessed via a remote control.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A diagnostic imaging method comprising:
    moving an x-ray source and an x-ray detector continuously along at least a segment of an ellipse selected to pass through or close to preferred or conventional coronary artery viewing angles;
    injecting a dose of a contrast agent;
    generating a multiplicity of contrast agent enhanced coronary projection images of a region of interest including coronary arteries during the moving of the x-ray source and x-ray detector, the multiplicity of projection images including a plurality of projection images at different angles through the region of interest; and
    selecting a plurality of the images generated along the elliptical trajectory.

2. The method according to claim 1, wherein the region-of-interest includes the left coronary system, the x-ray source and detector move continuously, and repeatedly along the trajectory, and views along at least four different viewing angles are selected and displayed.

3. The method according to claim 1, wherein the contrast agent is continuously injected into the subject during the movement of the x-ray source and detector along the trajectory and the generation of images.

4. The method according to claim 3, further including:
    repeatedly moving the x-ray source and detector along the trajectory when the contrast agent is at its peak and at least one of before and after the contrast agent is at its peak in the region-of-interest; and,
    displaying a plurality of images corresponding to a common viewing angle which illustrate time evolution of contrast agent.

5. The method according to claim 3, further including:
    displaying a multiplicity of the images generated along the trajectory in a ciné mode to simulate viewing of the region-of-interest while moving along the trajectory.

6. The method according to claim 3, further including:
    selecting a standardized trajectory; and
    customizing the standardized trajectory to pass through or close to one or more preferred coronary artery viewing angles.

7. The method according to claim 6, wherein customizing the standardized trajectory includes at least one of:
    warping the standardized trajectory out of a single plane,
    creating depressions in the standardized trajectory,
    creating deviations towards an exterior of the standardized trajectory.

8. The method according to claim 1, further including:
    as the radiation source and detector move along the trajectory, moving the radiation detector closer to and further from the subject.

9. A medical diagnostic imaging system which performs the imaging method according to claim 1.

10. A control processor programmed to control a mechanical arm x-ray imaging device to perform the method according to claim 1.

11. The method according to claim 1 wherein a single dose of the contrast agent is injected to generate the multiplicity of contrast agent enhanced coronary projection images.

12. A diagnostic imaging apparatus comprising:
    a means for defining an elliptical trajectory of viewing angles comprising at least a segment of an eclipse passing through or close to a plurality of coronary artery viewing angles;
    a means for moving an x-ray source and an x-ray detector continuously along the elliptical trajectory;
    a means for generating a multiplicity of projection images during the moving to generate a plurality of projection images at different angles through a region of interest including coronary arteries; and
    a means for selecting a plurality of the images generated along the elliptical trajectory.

13. The apparatus according to claim 12, further including:
    a means for repeatedly moving the x-ray source and detector along the elliptical trajectory when a contrast agent is at its peak and at least one of before and after the contrast agent is at its peak in the region-of-interest; and,
    a means for displaying a plurality of images corresponding to a common viewing angle which illustrate time evolution of contrast agent.

14. The apparatus according to claim 13, further including:
    a means for displaying a multiplicity of the images generated along the trajectory in a ciné mode to simulate viewing of the region-of-interest while moving along the trajectory.

15. The apparatus according to claim 13, wherein the means for defining an elliptical trajectory includes:
    a means for customizing the elliptical trajectory.

16. The apparatus according to claim 12, further including:
    means for moving the radiation detector closer to and further from the subject as the radiation source and detector move along the trajectory.

17. The apparatus according to claim 12, further including:
    A means for delivering a dose of a contrast agent such that the multiplicity of projection images include images with each of a plurality of amounts of contrast agent enhancement at each of the different angles through the region of interest.

18. A diagnostic imaging method employing a mechanical arm to image a coronary angiography patient at selected viewing positions defined by a cranial or caudal viewing angle and a left or right anterior oblique viewing angle, the method comprising:
    traversing a continuous trajectory of viewing positions including viewing positions having (i) both cranial and caudal viewing angles, and (ii) both left and right anterior oblique viewing angles by adjusting both the cranial or caudal viewing angle and the left or right anterior oblique viewing angle during the traversing;
    acquiring images of the coronary angiography patient during the traversing; and
    administering a single contrast agent injection, the traversing of the continuous trajectory and the acquiring of images during the traversing being performed in conjunction with the single contrast agent injection to provide a complete set of coronary angiography images.

19. The diagnostic imaging method as set forth in claim 18, wherein the trajectory is generally elliptical and passes through or near the four standard viewing positions for left coronary angiography.

* * * * *